(12) United States Patent
Tsuji et al.

(10) Patent No.: US 12,303,578 B2
(45) Date of Patent: May 20, 2025

(54) MOLDED BODY

(71) Applicant: HOYU CO., LTD., Aichi (JP)

(72) Inventors: Hinako Tsuji, Aichi (JP); Yuki Ito, Aichi (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 18/549,726

(22) PCT Filed: Mar. 17, 2022

(86) PCT No.: PCT/JP2022/012477
§ 371 (c)(1),
(2) Date: Sep. 8, 2023

(87) PCT Pub. No.: WO2022/196787
PCT Pub. Date: Sep. 22, 2022

(65) Prior Publication Data
US 2024/0156695 A1 May 16, 2024

(30) Foreign Application Priority Data
Mar. 17, 2021 (JP) ................ 2021-043745

(51) Int. Cl.
*A61Q 5/10* (2006.01)
*A61K 8/19* (2006.01)
*A61K 8/60* (2006.01)
*A61K 8/73* (2006.01)

(52) U.S. Cl.
CPC .................. *A61K 8/19* (2013.01); *A61K 8/60* (2013.01); *A61K 8/731* (2013.01); *A61K 8/732* (2013.01); *A61Q 5/10* (2013.01)

(58) Field of Classification Search
CPC . A61K 8/19; A61K 8/60; A61K 8/731; A61K 8/732; A61K 8/0216; A61K 8/345; A61Q 5/10

USPC ..................................................... 8/405, 524
See application file for complete search history.

(56) References Cited

U.S. PATENT DOCUMENTS

| 2006/0042027 | A1 | | 3/2006 | Schulze zur Wiesche et al. |
| 2011/0203604 | A1 | | 8/2011 | Hasegawa et al. |
| 2020/0093729 | A1 | * | 3/2020 | Mignon ............... A61K 8/8176 |

FOREIGN PATENT DOCUMENTS

| EP | 2361604 | A1 | | 8/2011 | |
| EP | 3473234 | A1 | * | 4/2019 | ............... A61Q 5/10 |
| FR | 3060333 | A1 | * | 6/2018 | ............... A61Q 5/10 |
| JP | S46-004280 | B | | 2/1971 | |
| JP | 2005-526737 | A | | 9/2005 | |
| JP | 2006273759 | A | * | 10/2006 | ............... A61Q 5/10 |
| JP | 2015-124176 | A | | 7/2015 | |

OTHER PUBLICATIONS

International Search Report dated May 31, 2022 filed in PCT/JP2022/012477.

* cited by examiner

*Primary Examiner* — Eisa B Elhilo
(74) *Attorney, Agent, or Firm* — Rankin, Hill & Clark LLP

(57) ABSTRACT

An object of the present invention is to provide a molded body having excellent stability of a percarbonate. In order to solve the above-described problem, there is provided a molded body that includes (A) a substance having a water absorbency of less than 106 in terms of a weight change rate, (B) a substance having a water absorbency of 106 or more in terms of a weight change rate, and (C) a percarbonate. According to the present invention, it is possible to provide a molded body in which stability of a percarbonate, solubility of a molded body in water, and moldability of a molded body are improved. In the molded body, it is preferable that (A) is at least one selected from the group consisting of cellulose, a cellulose derivative, and sugar alcohol, and (B) is at least one selected from starches.

10 Claims, No Drawings

MOLDED BODY

TECHNICAL FIELD

The present invention relates to a molded body. More particularly, the present invention relates to a molded body used in the field of cosmetics.

BACKGROUND ART

Oxidative hair dyes are known as cosmetics for dyeing human hair and the like. When an oxidative hair dye is applied to hair, the oxidation dye penetrates into the hair and then undergoes oxidative polymerization inside the hair to develop color. In an oxidative hair dye, an oxidation dye polymer is formed. Therefore, the dye easily stays inside the hair, and the hair dyed state is maintained for a long period of time as compared with a temporary hair dye (hair colorant).

A bleaching/decoloring agent is also known as cosmetics for bleaching/decoloring human hair or the like. The bleaching/decoloring agent contains an oxidizing agent as an active ingredient and exerts bleaching/decoloring effects by the oxidizing agent decomposing a melanin pigment inside hair or a dye fixed in hair through hair coloring.

Examples of the dosage form of a hair dye and a bleaching/decoloring agent which contain an oxidizing agent include a solid, a liquid, and an aerosol. As a hair dye and a bleaching/decoloring agent which are solid molded bodies, Patent Literature 1 discloses a molded body that contains a carrier, a dissolution accelerator, and an oxidation dye precursor. Also, Patent Literature 2 discloses a multiple tablet hair dye including an inert substance in an intermediate layer between a hair dye component and an oxidizing agent.

CITATION LIST

Patent Literature

Patent Literature 1: JP-T-2005-526737
Patent Literature 2: JP-B-46-4280

SUMMARY OF INVENTION

Problems to be Solved by Invention

The hair dye and the bleaching/decoloring agent, which are molded bodies, have not only high storage stability of the components but also high transport efficiency. However, these molded bodies have problems in that solubility in water decreases when they are blended to impart thickening properties necessary for application to hair and to improve fluidity and moldability in tableting. Furthermore, the present inventors have found that the stability of a percarbonate is reduced by forming a molded body. Therefore, it is desired to develop a molded body used for hair dyeing and bleaching/decoloring which has excellent moldability and solubility and improved stability of a percarbonate.

Therefore, an object of the present invention is to provide a molded body having excellent moldability and solubility and improved stability of a percarbonate.

Solution to Problems

The present inventors have extensively conducted studies on the above-mentioned problems and resultantly found that a molded body having excellent stability of a percarbonate can be obtained by blending (A) a substance having a water absorbency of less than 106 in terms of a weight change rate, (B) a substance having a water absorbency of 106 or more in terms of a weight change rate, and (C) a percarbonate. Thus, the present invention has been completed.

That is, the present invention provides the following [1] to [4].

[1] A molded body including the following components (A) to (C):
  (A) a substance having a water absorbency of less than 106 in terms of a weight change rate;
  (B) a substance having a water absorbency of 106 or more in terms of a weight change rate; and
  (C) a percarbonate.

According to this molded body, the effects of improving the stability of the component (C), the solubility of the molded body in water, and the moldability of the molded body can be exhibited by the actions of the components (A) and (B).

[2] The molded body according to [1], in which a ratio (A)/(C) of a content of the component (A) to a content of the component (C) is 0.1 to 4.00.

According to this feature, the effect of improving the stability of the component (C) and the moldability of the molded body can be further exhibited by controlling the content ratio of the component (A) and the component (C) contained in the molded body.

[3] The molded body according to [1] or [2], in which a ratio (B)/(C) of a content of the component (B) to a content of the component (C) is 0.1 to 4.00.

According to this feature, the effect of improving the stability of the component (C) and the solubility of the molded body in water can be further exhibited by controlling the content ratio of the component (B) and the component (C) contained in the molded body.

[4] The molded body according to [1] to [3], in which a ratio ((A)+(B))/(C) of a sum of contents of the component (A) and the component (B) to a content of the component (C) is 0.3 to 8.0.

According to this feature, the effect of improving the stability of the component (C), the solubility of the molded body in water, and the moldability of the molded body can be further exhibited by controlling the contents of the component (A), the component (B), and the component (C) contained in the molded body.

Effects of Invention

According to the present invention, it is possible to provide a molded body which is excellent in stability of the percarbonate (C), solubility of the molded body, and moldability of the molded body, by blending (A) a substance having a water absorbency of less than 106 in terms of a weight change rate and (B) a substance having a water absorbency of 106 or more in terms of a weight change rate into the molded body.

DESCRIPTION OF EMBODIMENTS

Hereinafter, an embodiment of a molded body according to the present invention will be described in detail.

The molded body described in the embodiment is merely exemplified for describing the molded body according to the present invention, and the molded body is not limited thereto.

The molded body of the present invention is a solid body molded into a desired shape. The shape is not particularly limited, and examples thereof include a disk shape, a cylindrical shape, a prismatic shape, and a spherical shape.

The method for producing the molded body of the present invention is not particularly limited. For example, the molded body can be produced by directly tableting mixed components and additives or by mixing granulated components and additives and tableting the mixture. In addition, granular particles can also be produced by a pan type granulating machine or a rolling granulating machine. Also, a flake shape may be formed by a compression molding machine such as a roller compactor. From the viewpoint of improving the strength and productivity of the molded body, the molded body is preferably a tableted product formed by tableting.

The molded body of the present invention is used by being dissolved in an aqueous solution such as water when used as a hair dye or a bleaching/decoloring agent. The molded body contains (A) a substance having a water absorbency of less than 106 in terms of a weight change rate, (B) a substance having a water absorbency of 106 or more in terms of a weight change rate, and (C) a percarbonate. By blending the component (A) and the component (B) in the molded body, it is possible to exhibit effects of improving the stability of the percarbonate as the component (C), the solubility of the molded body in an aqueous solution, and the moldability of the molded body.

The water absorbency used herein is measured by using a predetermined amount as an initial sample, measuring the mass of a post-moisture absorption sample 24 hours after allowed to stand under conditions of a temperature of 30° C. and a relative humidity of 80%, and dividing the weight of the post-moisture absorption sample by the weight of the initial sample (weight change rate).

The shape of the molded body is not particularly limited, and examples thereof include circular tablets, elliptical tablets, and flower-shaped tablets. Further, the molded body can be provided with one or more sectioning lines for dividing the molded body into two, four, or the like as necessary.

The size of the molded body is not particularly limited, and for example, the diameter is 5 mm or more and 50 mm or less. The lower limit is more preferably 10 mm or more, further preferably 15 mm or more, and particularly preferably 20 mm or more. On the other hand, the upper limit is more preferably 40 mm or less, further preferably 35 mm or less, and particularly preferably 30 mm or less.

The thickness of the molded body is not particularly limited and is, for example, 1.0 mm or more and 20.0 mm or less. The lower limit is more preferably 2.0 mm or more, further preferably 2.5 mm or more, and particularly preferably 3.0 mm or more. On the other hand, the upper limit is more preferably 15.0 mm or less, further preferably 12.0 mm or less, and particularly preferably 10.0 mm or less.

By setting the size and thickness of the molded body within the above-described ranges, the molded body has a size that allows easy adjustment of the amount when used as a hair dye or a bleaching/decoloring agent, and it is possible to easily reduce the amount of an unused chemical agent after hair treatment and to easily add a chemical agent during hair treatment.

In addition, by setting the size of the molded body to 20.0 mm or more, it is possible to prevent accidental ingestion by children, elderly people, and the like.

Next, a method for producing a molded body will be described.

As a method for producing a molded body, a usual method used in technical fields such as cosmetics, quasi-drugs, and pharmaceuticals can be used. As a step of producing a molded body, mixed components and additives may be directly tableted, or granulated components and additives may be mixed and tableted.

The granulation method is not particularly limited, and examples thereof include a dry granulation method, a fluidized bed granulation method, a rolling granulation method, a stirring granulation method, and a spray granulation method.

The mixer used in the mixing step is not particularly limited, and examples thereof include a tumbler mixer, a V-type mixer, a double cone mixer, and an infinite mixer.

The tableting machine used in the tableting step is not particularly limited, and examples thereof include a single tableting machine and a rotary tableting machine.

Next, the components contained in the molded body of the present invention will be described in detail.

<(A) Substance Having Water Absorbency of Less than 106>

A substance having a water absorbency of less than 106 as a component (A) improves stability of a percarbonate contained in a molded body and moldability of a molded body. The lower limit is preferably 100 or more and more preferably 105 or more, from the viewpoint of improving moldability.

Such a substance is not particularly limited as long as it has a water absorbency of less than 106 and is acceptable for applications such as foods, cosmetics, quasi-drugs, and pharmaceuticals. Examples thereof include cellulose, cellulose derivatives, and sugar alcohol.

Cellulose and cellulose derivatives are not particularly limited as long as they are polymer compounds having a structure in which a large number of 3-glucoses are linearly polymerized by glycoside bonds and as long as they are acceptable for applications such as foods, cosmetics, quasi-drugs, and pharmaceuticals.

Specific examples of cellulose and cellulose derivatives include crystalline cellulose, low substituted hydroxypropyl cellulose, hydroxypropyl cellulose, hydroxypropyl methyl cellulose, hydroxyethyl cellulose, carboxymethyl cellulose, and croscarmellose.

The sugar alcohol is not particularly limited as long as it is a sugar in which carbonyl groups of aldoses and ketoses are reduced and as long as it is acceptable for applications such as foods, cosmetics, quasi-drugs, and pharmaceuticals.

Specific examples of the sugar alcohol include mannitol, sorbitol, maltitol, xylitol, erythritol, lactitol, and glycerin.

Preferred examples of the component (A) include mannitol and crystalline cellulose and more preferably crystalline cellulose, from the viewpoint of improving the stability of the percarbonate and the moldability of the molded body. These components (A) may be blended individually or may be blended in combination of two or more thereof.

The content of the component (A) is not particularly limited and is, for example, 0.5 mass % or more and 50.0 mass % or less with respect to the mass of the molded body. The lower limit is more preferably 1.0 mass % or more, further preferably 5.0 mass % or more, particularly preferably 10.0 mass % or more, and most preferably 12.0 mass % or more. On the other hand, the upper limit is more preferably 45.0 mass % or less, further preferably 43.0 mass % or less, and particularly preferably 40.0 mass % or less.

By setting the content of the component (A) in the molded body within the above-described range, a molded body having improved moldability of the molded body can be obtained.

<(B) Substance Having Water Absorbency of More than 106>

A substance having a water absorbency of 106 or more as a component (B) improves stability of a percarbonate contained in a molded body and solubility of a molded body. The lower limit is preferably 107 or more and more preferably 112 or more, from the viewpoint of improving solubility. The upper limit is preferably 120 or less and more preferably 115 or less.

Such a substance is not particularly limited as long as it has a water absorbency of 106 or more and is acceptable for applications such as foods, cosmetics, quasi-drugs, and pharmaceuticals. An example thereof is starches.

The starches are not particularly limited as long as they are polymer compounds having a structure in which a large number of a-glucose molecules are polymerized by glycoside bonds and as long as they are acceptable for applications such as foods, cosmetics, quasi-drugs, and pharmaceuticals.

Specific examples of the starches include acetic acid starch, oxidized starch, potato starch, corn starch, rice starch, wheat starch, sweet potato starch, tapioca starch, hydroxypropylated phosphoric acid crosslinked starch, acetylated adipic acid crosslinked starch, acetylated phosphoric acid crosslinked starch, acetylated oxidized starch, starch sodium octenylsuccinate, hydroxypropyl starch, phosphoric acid monoesterified phosphoric acid crosslinked starch, phosphorylated starch, and D-glucose.

Preferred examples of the component (B) include acetic acid starch, potato starch, hydroxypropylated phosphoric acid crosslinked starch, corn starch, rice starch, and D-glucose, more preferably acetic acid starch and potato starch, and further preferably acetic acid starch, from the viewpoint of improving the stability of the percarbonate and the solubility of the molded body. These components (B) may be blended individually or may be blended in combination of two or more thereof.

The content of the component (B) is not particularly limited and is, for example, 0.5 mass % or more and 50.0 mass % or less with respect to the mass of the molded body. The lower limit is more preferably 1.0 mass % or more, further preferably 5.0 mass % or more, particularly preferably 10.0 mass % or more, and most preferably 13.0 mass % or more. On the other hand, the upper limit is more preferably 45.0 mass % or less, further preferably 43.0 mass % or less, and particularly preferably 40.0 mass % or less.

By setting the content of the component (B) in the molded body within the above-described range, a molded body having improved stability of the percarbonate and improved solubility of the molded body can be obtained.

<(C) Percarbonate>

A percarbonate as a component (C) has an action of oxidizing an oxidation dye to develop color and an action of decomposing melanin inside hair.

The percarbonate is not particularly limited as long as it generates hydrogen peroxide by being dissolved in water and is acceptable for applications such as cosmetics, quasi-drugs, and pharmaceuticals.

Specific examples of the percarbonate include sodium percarbonate, potassium percarbonate, calcium percarbonate, magnesium percarbonate, and ammonium percarbonate.

Preferable examples of the component (C) include sodium percarbonate and potassium percarbonate from the viewpoint of improving hair dyeability and a bleaching/decoloring action. These percarbonates may be blended individually or may be blended in combination of two or more thereof.

The content of the percarbonate is not particularly limited and is, for example, 5 mass % or more and 40 mass % or less with respect to the mass of the molded body. The lower limit is more preferably 7 mass % or more, further preferably 9 mass % or more, and particularly preferably 10 mass % or more. On the other hand, the upper limit is more preferably 38 mass % or less, further preferably 36 mass % or less, and particularly preferably 35 mass % or less.

By setting the content of the percarbonate in the molded body within the above-described range, a molded body having improved hair dyeability and an improved bleaching/decoloring action can be obtained.

A ratio (A)/(C) of a content of the component (A) to a content of the component (C) in the molded body is not particularly limited and is, for example, 0.01 or more and 5.0 or less. The lower limit is more preferably 0.1 or more, further preferably 0.3 or more, particularly preferably 0.5 or more, and most preferably 1.0 or more. On the other hand, the upper limit is more preferably 4.5 or less and further preferably 4.0 or less.

By setting the ratio (A)/(C) of the content of the component (A) to the content of the component (C) in the molded body within the above-described range, the stability of the percarbonate and the moldability of the molded body can be further improved.

A ratio (B)/(C) of a content of the component (B) to a content of the component (C) in the molded body is not particularly limited and is, for example, 0.01 or more and 5.0 or less. The lower limit is more preferably 0.1 or more, further preferably 0.3 or more, particularly preferably 0.5 or more, and most preferably 1.0 or more. On the other hand, the upper limit is more preferably 4.5 or less and further preferably 4.0 or less.

By setting the ratio (B)/(C) of the content of the component (B) to the content of the component (C) in the molded body within the above-described range, the stability of the percarbonate and the solubility of the molded body can be further improved.

A ratio ((A)+(B))/(C) of a sum of contents of the component (A) and the component (B) to a content of the component (C) in the molded body is not particularly limited and is, for example, 0.05 or more and 9.0 or less. The lower limit is more preferably 0.3 or more, further preferably 0.5 or more, particularly preferably 1.0 or more, and most preferably 2.0 or more. On the other hand, the upper limit is more preferably 8.5 or less and further preferably 8.0 or less.

By setting the ratio ((A)+(B))/(C) of the sum of the contents of the component (A) and the component (B) to the content of the component (C) in the molded body within the above-described range, the stability of the percarbonate, the solubility of the molded body, and the moldability of the molded body can be further improved.

<Other Components>

The molded body of the present invention may contain other components as necessary in addition to the components (A) to (C). Specific examples of the component to be added include (D) an oxidation dye, (E) a lubricant, (F) a thickener, a chelating agent, a hydrogen peroxide stabilizer, a pH adjuster, an excipient, a binder, a disintegrant, a stabilizer, a preservative, a fragrance, a direct dye, and a colorant.

(Oxidation Dye)

An oxidation dye as a component (D) is a dye that develops color by being oxidatively polymerized by an oxidizing agent. The oxidation dye includes a dye intermediate and a coupler. The dye intermediate is a substance that develops color by its own oxidation, and the coupler is a substance that produces various color tones by combination with the dye intermediate.

Examples of the dye intermediate include p-phenylenediamine, toluene-2,5-diamine(p-toluylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chlor-p-phenylenediamine, 4-amino-m-cresol, 2-amino-4-hydroxyethylaminoani sole, 2,4-diaminophenol, and salts thereof. One or two or more of these dye intermediates can be selected and used.

The coupler develops color by binding to the dye intermediate. Examples of the coupler include resorcin, 5-amino-o-cresol, m-aminophenol, a-naphthol, 5-(2-hydroxyethyl-amino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, 1,5-dihydroxynaphthalene, and salts thereof. Further, an example of 2,4-di aminophenoxyethanol is 2,4-diaminophenoxyethanol hydrochloride. One or two or more of these couplers can be selected and used. Also, for example, an oxidation dye listed in "The Japanese Standards of Quasi-drug Ingredients" (Yakuji Nippo Co., Ltd., published in June, 2006) may be appropriately contained.

The content of the oxidation dye in a solution after the molded body is dissolved in water or the like is not particularly limited and can be, for example, within a range of 0.01 to 10 mass %, preferably within a range of 0.1 to 7 mass %, and more preferably within a range of 0.5 to 5 mass %.

(Lubricant)

A lubricant as a component (E) is not particularly limited as long as it reduces the adhesive force of a powder component to enhance fluidity and is acceptable for applications such as cosmetics, quasi-drugs, pharmaceuticals, and foods. Examples thereof include phyllosilicate mineral powder, silicon oxide, saturated fatty acid, esters, waxes, hardened vegetable oil, fat, and polyether.

Specific examples of the lubricant include talc, light anhydrous silicic acid, magnesium stearate, calcium stearate, sucrose fatty acid ester, magnesium carbonate, sodium benzoate, palmitic acid, sodium stearyl fumarate, beeswax, soybean hardened oil, cocoa butter, and polyethylene glycol. These lubricants may be blended individually or may be blended in combination of two or more thereof.

By adding the lubricant, occurrence of tableting failure such as sticking can be suppressed during production of the molded body. The content of the lubricant is not particularly limited and is, for example, 0.1 mass % or more and 5.0 mass % or less with respect to the mass of the molded body.

(Thickener)

A thickener as a component (F) is not particularly limited as long as it has viscosity and solubility in moisture and is acceptable for applications such as cosmetics, quasi-drugs, pharmaceuticals, and foods. Examples thereof include polysaccharides and water-soluble acrylic acid polymers.

Specific examples of the thickener include xanthan gum, sodium alginate, guar gum, cationized guar gum such as O-[2-hydroxy-3-(trimethylammonio)propyl] guar gum chloride, a carboxyvinyl polymer, carrageenan, gellan gum, pectin, gum arabic, and locust bean gum. These thickeners may be blended individually or may be blended in combination of two or more thereof. The viscosity of the thickener can be measured by a capillary viscometer method described in the Japanese Pharmacopoeia, 17th Edition, or the like.

By adding the thickener, the moldability of the molded body can be improved, and viscosity can be imparted to an aqueous solution in which the molded body is dissolved. The content of the thickener is not particularly limited and is, for example, 0.1 mass % or more and 20.0 mass % or less with respect to the mass of the molded body.

(Chelating Agent)

The chelating agent is not particularly limited as long as it inactivates a metal ion and is acceptable for applications such as cosmetics, quasi-drugs, and pharmaceuticals. An example thereof is that having a ligand and binding a metal ion.

Specific examples of the chelating agent include ethylenediaminetetraacetic acid (EDTA, edetic acid), hydroxyethylethylenediaminetriacetic acid (HEDTA) and salts thereof, diethylenetriaminepentaacetic acid and salts thereof, and hydroxyethanediphosphonic acid (HEDP, etidronic acid) and salts thereof. These chelating agents may be blended individually or may be blended in combination of two or more thereof.

By adding the chelating agent, the solubility of the molded article can be improved.

(pH Adjuster)

The pH adjuster is not particularly limited as long as it adjusts the pH of a composition and is acceptable for applications such as cosmetics, quasi-drugs, and pharmaceuticals. Examples thereof include inorganic acid, organic acid, inorganic alkali, and organic alkali.

Specific examples of the organic acid include hydroxycarboxylic acids such as glycolic acid, lactic acid, malic acid, citric acid, and tartaric acid, and dicarboxylic acids such as succinic acid.

Specific examples of the organic alkali include volatile alkali components such as morpholine, alkanolamines such as monoethanolamine, amino alcohols such as 2-amino-2-methyl-1-propanol, and basic amino acids such as L-arginine, L-lysine, and L-histidine. These pH adjusters may be blended individually or may be blended in combination of two or more thereof.

By adding the pH adjuster, the hair dyeability, bleaching/decoloring action, and safety can be improved when the molded body is used as a hair dye or a bleaching/decoloring agent.

(Excipient)

The excipient is not particularly limited as long as it adjusts the bulk of the molded body and is acceptable for applications such as cosmetics, quasi-drugs, pharmaceuticals, and foods. Examples thereof include saccharides, phosphates, and sulfates.

Specific examples of the excipient include lactose, white sugar, glucose, calcium phosphate, and calcium sulfate. These excipients may be blended individually or may be blended in combination of two or more thereof.

By adding the excipient, the size of the molded body can be adjusted.

(Binder)

The binder is not particularly limited as long as it increases the binding force of a powder component and is acceptable for applications such as cosmetics, quasi-drugs, and pharmaceuticals. Examples thereof include synthetic resins, saccharides, polyethers, and waxes.

Specific examples of the binder include polyvinylpyrrolidone, polyvinyl alcohol, polyacrylic acid, polymethacrylic acid, glucose, maltose, lactose, white sugar, dextrin, polyethylene glycol, paraffin, gelatin, agar, and pullulan. These binders may be blended individually or may be blended in combination of two or more thereof.

By adding the binder, a binding force is imparted to the powder component, and a stable molded body can be produced.

(Disintegrant)

The disintegrant is not particularly limited as long as it disintegrates tablets and is acceptable for applications such as cosmetics, quasi-drugs, pharmaceuticals, and foods. Examples thereof include saccharides and synthetic resins.

Specific examples of the disintegrant include white sugar, dextrin, and polyvinylpyrrolidone. These disintegrants may be blended individually or may be blended in combination of two or more thereof.

By adding the disintegrant, disintegration of the molded body can be promoted, and solubility in an aqueous solution such as water can be improved.

(Stabilizer)

The stabilizer is not particularly limited as long as it suppresses chemical decomposition and physical decomposition of an active ingredient and is acceptable for applications such as cosmetics, quasi-drugs, and pharmaceuticals. Examples thereof include inorganic compounds, organic acids, organic acid salts, and vitamins.

Specific examples of the stabilizer include sodium bisulfite, ascorbic acid, sodium edetate, and tocopherol. These stabilizers may be blended individually or may be blended in combination of two or more thereof.

By adding the stabilizer, the deactivation of the active ingredient contained in the molded body can be suppressed.

(Preservative)

The preservative is not particularly limited as long as it suppresses the growth of microorganisms or the like and is acceptable for applications such as cosmetics, quasi-drugs, and pharmaceuticals. Examples thereof include benzoates and paraoxybenzoic acid esters.

Specific examples of the preservative include sodium benzoate, propyl parahydroxybenzoate, methylparaben, and propylparaben. These preservatives may be blended individually or may be blended in combination of two or more thereof.

By adding the preservative, the molded body can be prevented from being contaminated with microorganisms.

(Fragrance)

The fragrance is not particularly limited as long as it improves the sensory sensation by a sense of smell of the molded body and is acceptable for applications such as cosmetics, quasi-drugs, and pharmaceuticals. Examples thereof include esters, alcohols, aldehydes, ketones, acetals, phenols, ethers, lactones, furans, and natural products.

Specific examples of the fragrance include lavender oil, orange oil, lemon oil, rose oil, spearmint oil, peppermint oil, cinnamon oil, fruit essence, benzaldehyde, neral, decanal, tolylaldehyde, 2-dodenal, geraniol, terpineol, hydroxycitronellal, nerol, nonanal, acetylcedrene, undecanal, eugenol, geraniol, jasmine lactone, citral, damascone, damasenone, γ-terpinene, vanillin, aldehyde C-8, aldehyde C-9, aldehyde C-12, and 2,6-dimethyloctanal. These fragrances may be blended individually or may be blended in combination of two or more thereof.

By adding the fragrance, a scent can be imparted to the molded body to enhance the palatability.

(Direct Dye)

The direct dye is not particularly limited as long as it has a color that adheres to or permeates into hair to dye the hair and is acceptable for applications such as cosmetics, quasi-drugs, and pharmaceuticals. Examples thereof include acidic dyes, basic dyes, natural dyes, nitro dyes, HC dyes, and disperse dyes. These direct dyes may be blended individually or may be blended in combination of two or more thereof.

Specific examples of the basic dye include Basic Blue 3, Basic Blue 6, Basic Blue 7, Basic Blue 9, Basic Blue 26, Basic Blue 41, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 2, Basic Red 22, Basic Red 46, Basic Red 51, Basic Red 76, Basic Red 118, Basic Violet 1, Basic Violet 3, Basic Violet 4, Basic Violet 10, Basic Violet 11:1, Basic Violet 14, Basic Violet 16, Basic Yellow 11, Basic Yellow 28, Basic Yellow 57, and Basic Yellow 87.

Specific examples of the natural dye include *gardenia* pigment, turmeric pigment, annatto pigment, sodium copper chlorophyllin, paprika pigment, lac pigment, and henna.

Specific examples of the nitro dye include 4-nitro-o-phenylenediamine, 2-nitro-p-phenylenediamine, 2-amino-4-nitrophenol, 2-amino-5 nitrophenol, picramic acid, picric acid, and salts thereof.

Specific examples of the HC dye include HC Blue No. 2, HC Blue No. 5, HC Blue No. 6, HC Blue No. 9, HC Blue No. 10, HC Blue No. 11, HC Blue No. 12, HC Blue No. 13, HC Orange No. 1, HC Orange No. 2, HC Orange No. 3, HC Red No. 1, HC Red No. 3, HC Red No. 7, HC Red No. 10, HC Red No. 11, HC Red No. 13, HC Red No. 14, HC Violet No. 1, HC Violet No. 2, HC Yellow No. 2, HC Yellow No. 4, HC Yellow No. 5, HC Yellow No. 6, HC Yellow No. 9, HC Yellow No. 10, HC Yellow No. 11, HC Yellow No. 12, HC Yellow No. 13, HC Yellow No. 14, and HC Yellow No. 15.

Specific examples of the disperse dye include Disperse Black 9, Disperse Blue 1, Disperse Blue 3, Disperse Blue 7, Disperse Brown 4, Disperse Orange 3, Disperse Red 11, Disperse Red 15, Disperse Red 17, Disperse Violet 1, Disperse Violet 4, and Disperse Violet 15.

By adding the direct dye, the hair dyeability of the molded body can be improved.

(Colorant)

The colorant is not particularly limited as long as it improves the palatability and distinguishability of the molded body and is acceptable for applications such as cosmetics, quasi-drugs, and pharmaceuticals. Examples thereof include natural pigments and synthetic pigments.

Specific examples of the colorant include edible synthetic colorants such as cochineal, carmine, curcumin, riboflavin, annatto, titanium oxide, yellow iron sesquioxide, iron sesquioxide, talc, calcined silica, magnesium carbonate, edible blue No. 1, edible blue No. 2, edible yellow No. 4, edible yellow No. 5, edible green No. 3, edible red No. 2, edible red No. 3, edible red No. 102, edible red No. 104, edible red No. 105, and edible red No. 106. These colorants may be blended individually or may be blended in combination of two or more thereof.

By adding the colorant, the molded body can be colored to enhance the palatability and distinguishability.

Examples of other additives include a solubilizing agent, a surfactant, a plasticizer, an emulsifier, a brightener, a foaming agent, a moisture-proof agent, a rot-proof agent, a fluidizing agent, a flavoring agent, a perfume, a disintegration aid, and an ultraviolet absorber. These additives may be blended individually or may be blended in combination of two or more thereof.

According to the above-described feature, the molded body of the present invention can exhibit the effects of improving the stability of the percarbonate, the solubility of the molded body, and the moldability of the molded body.

EXAMPLES

Hereinafter, the present invention will be specifically described with reference to Examples, but the technical scope of the present invention is not limited by these Examples.
(Composition of Each Agent)

Powder hair dye compositions and molded bodies (tablets) which contain the respective components shown in Tables 1 to 6 were prepared. The molded bodies were tableted with a particle weight of 2 g, a diameter of 20 mm, and a pressure of 20 KN. The numerical value in the column indicating each component in each table denotes the content of the component in the column, and the unit is mass %. The notations "(A)" to "(F)" in the tables respectively denote compounds corresponding to the components (A) to (F) described in the claims and the specification of the present application. Also, the measurement results of the water absorbency of the components (A) and (B) used in an experiment are shown in Table 1.
(Measurement of Water Absorbency)

For water absorbency, a predetermined amount was used as an initial sample, the mass of a post-moisture absorption sample was measured 24 hours after allowed to stand under conditions of a temperature of 30° C. and a relative humidity of 80%, and the weight change rate calculated by dividing the weight of the post-moisture absorption sample by the weight of the initial sample was defined as water absorbency. The water absorbencies of the components (A) and (B) are shown in Table 1.

TABLE 1

| | Compound name | Water absorbency |
|---|---|---|
| Component (A) | Crystalline cellulose | 105 |
| | Mannitol | 100 |
| Component (B) | Acetic acid starch | 113 |
| | Potato starch | 116 |
| | Hydroxypropylated phosphoric acid crosslinked starch | 111 |
| | Corn starch | 107 |
| | Rice starch | 110 |
| | D-Glucose | 123 |

(Stability Evaluation of Sodium Percarbonate)

The stability of sodium percarbonate was evaluated by the magnitude of the change in color tone of dyed hair before and after storage.

Two grams of the powder hair dye composition of each of Examples and Comparative Examples and 10 mL of water were put into a 100 mL mixing container and mixed using a stirring rod to prepare a hair dye coating solution. Three grams of the obtained hair dye coating solution was applied on 1 g of a white hair bundle using a brush, and the hair bundle was left to stand for 40 minutes after the application operation to perform a hair dyeing treatment. The hair bundle subjected to the hair dyeing treatment was subjected to water washing and shampoo washing to wash the hair dye coating solution off and treated with a conditioner. Thereafter, moisture was wiped off with a towel, and the hair bundle was dried with a dryer.
(Evaluation of Effect of Suppressing Change in Color Tone of Dyed Hair)

The powder hair dye composition of each example was stored in a thermostatic bath at 50° C. and a humidity of 80% for 60 days. Using the powder composition of each example stored for the predetermined period, a hair dyeing treatment was performed by the above-described hair dyeing treatment method to obtain each hair bundle. In addition, for the powder hair dye composition of each example not subjected to the storage treatment, each hair bundle was prepared by performing the hair dyeing treatment in the same manner and used as a control.

For each of the obtained hair bundles, the presence or absence of a change in color tone (brightness and saturation) of dyed hair depending on the presence or absence of the storage treatment was visually observed by 10 panelists under a standard light source and evaluated according to the following criteria.
(Evaluation Criteria)

Scoring was performed in five stages of almost no change in color tone of dyed hair (5 points), slight change in color tone of dyed hair (4 points), some change in color tone of dyed hair (3 points), change in color tone of dyed hair (2 points), and large change in color tone of dyed hair (1 point).

Next, an average value was calculated for the scoring results of the individual panelists, and an average value of 4.6 points or more was evaluated as "excellent: 5", 3.6 points or more and less than 4.6 points as "good: 4", 2.6 points or more and less than 3.6 points as "acceptable: 3", 1.6 points or more and less than 2.6 points as "somewhat poor: 2", and 1.0 point or more and less than 1.6 points as "poor: 1".
(Evaluation of Solubility in Water)

The solubility test of the molded body was performed by placing one molded body in 10 mL of water, allowing the molded body to stand for 3 seconds, and thereafter visually confirming the solubility when the molded body was stirred with a brush.

In the evaluation of solubility of the molded body, "5" was assigned when dissolved within 5 seconds, "4" in 5 seconds or more and less than 10 seconds, "3" in 10 seconds or more and less than 20 seconds, "2" in 20 seconds or more and less than 30 seconds, and "1" in 30 seconds or more.
(Evaluation of Moldability of Molded Body)

The moldability test of the molded body was performed by visually confirming the state of the prepared sample.

In the evaluation of moldability of the molded body, "5" was assigned when the sample surface has no chips, "4" was assigned when the sample surface has one small chip, "3" was assigned when the sample surface has two or more small chips, "2" was assigned when the sample surface has one or more large chips, and "1" was assigned when a molded body was not formed with the powdery state remained.

TABLE 2

| | Component name | Example 1 | Example 2 | Comparative Example 1 | Comparative Example 2 | Comparative Example 3 |
|---|---|---|---|---|---|---|
| (A) | Crystalline cellulose | 20.0 | 20.0 | — | — | 40.0 |
| (B) | Acetic acid starch | 20.0 | 20.0 | — | 40.0 | — |
| (C) | Sodium percarbonate | 16.5 | 16.5 | 16.5 | 16.5 | 16.5 |
| (D) | p-Phenylenediamine sulfate | 13.0 | 13.0 | 13.0 | 13.0 | 13.0 |

TABLE 2-continued

|  | Component name | Example 1 | Example 2 | Comparative Example 1 | Comparative Example 2 | Comparative Example 3 |
|---|---|---|---|---|---|---|
|  | Toluene-2,5-diamine sulfate | 3.0 | 3.0 | 3.0 | 3.0 | 3.0 |
|  | m-Aminophenol sulfate | 1.0 | 1.0 | 1.0 | 1.0 | 1.0 |
| (E) | Magnesium stearate | 0.5 | 0.5 | 0.5 | 0.5 | 0.5 |
| (F) | Xanthan gum | 3.0 | — | 3.0 | 3.0 | 3.0 |
|  | Sodium carboxymethyl cellulose | 5.0 | — | 5.0 | 5.0 | 5.0 |
|  | Sodium sulfate | 15.7 | 23.7 | 55.7 | 15.7 | 15.7 |
|  | O-[2-Hydroxy-3-(trimethylammonio)propyl] guar gum chloride | 1.0 | 1.0 | 1.0 | 1.0 | 1.0 |
|  | Trisodium hydroxyethyl ethylenediamine triacetate dihydrate | 1.0 | 1.0 | 1.0 | 1.0 | 1.0 |
|  | Fragrance | 0.3 | 0.3 | 0.3 | 0.3 | 0.3 |
|  | Total (mass %) | 100.0 | 100.0 | 100.0 | 100.0 | 100.0 |
|  | A/C | 1.212 | 1.212 | — | — | 2.424 |
|  | B/C | 1.212 | 1.212 | — | 2.424 | — |
|  | (A + B)/C | 2.424 | 2.424 | — | — | — |
|  | Stability evaluation of sodium percarbonate | 5 | 4 | 1 | 4 | 3 |
|  | Solubility evaluation in water | 5 | 5 | 4 | 5 | 1 |
|  | Moldability evaluation of molded body | 5 | 4 | 3 | 1 | 4 |

Table 2 illustrates that in comparison between Examples 1 and 2 and Comparative Examples 1 to 3, Examples 1 and 2, which contain the component (A) and the component (B), had a rating of 4 or more in all of the stability evaluation, solubility evaluation, and moldability evaluation, while Comparative Examples 1 to 3, which do not contain at least one of the component (A) and the component (B), had a rating of 1 in one of the stability evaluation, solubility evaluation, and moldability evaluation.

Therefore, it was demonstrated that the stability of the percarbonate contained in the molded body, the solubility of the molded body, and the moldability of the molded body are all improved by blending the component (A) and the component (B) in the molded body.

TABLE 3

|  | Component name | Example 1 | Example 3 | Example 4 | Example 5 | Example 6 | Example 7 | Example 8 |
|---|---|---|---|---|---|---|---|---|
| (A) | Crystalline cellulose | 20.0 | — | 20.0 | 20.0 | 20.0 | 20.0 | 20.0 |
|  | Mannitol | — | 20.0 | — | — | — | — | — |
| (B) | Acetic acid starch | 20.0 | 20.0 | — | — | — | — | — |
|  | Potato starch | — | — | 20.0 | — | — | — | — |
|  | Hydroxypropylated phosphoric acid crosslinked starch | — | — | — | 20.0 | — | — | — |
|  | Corn starch | — | — | — | — | 20.0 | — | — |
|  | Rice starch | — | — | — | — | — | 20.0 | — |
|  | D-Glucose | — | — | — | — | — | — | 20.0 |
| (C) | Sodium percarbonate | 16.5 | 16.5 | 16.5 | 16.5 | 16.5 | 16.5 | 16.5 |
| (D) | p-Phenylenediamine sulfate | 13.0 | 13.0 | 13.0 | 13.0 | 13.0 | 13.0 | 13.0 |
|  | Toluene-2,5-diamine sulfate | 3.0 | 3.0 | 3.0 | 3.0 | 3.0 | 3.0 | 3.0 |
|  | m-Aminophenol sulfate | 1.0 | 1.0 | 1.0 | 1.0 | 1.0 | 1.0 | 1.0 |
| (E) | Magnesium stearate | 0.5 | 0.5 | 0.5 | 0.5 | 0.5 | 0.5 | 0.5 |
| (F) | Xanthan gum | 3.0 | 3.0 | 3.0 | 3.0 | 3.0 | 3.0 | 3.0 |
|  | Sodium carboxymethyl cellulose | 5.0 | 5.0 | 5.0 | 5.0 | 5.0 | 5.0 | 5.0 |
|  | Sodium sulfate | 15.7 | 15.7 | 15.7 | 15.7 | 15.7 | 15.7 | 15.7 |
|  | O-[2-Hydroxy-3-(trimethylammonio)propyl] guar gum chloride | 1.0 | 1.0 | 1.0 | 1.0 | 1.0 | 1.0 | 1.0 |
|  | Trisodium hydroxyethyl ethylenediamine triacetate dihydrate | 1.0 | 1.0 | 1.0 | 1.0 | 1.0 | 1.0 | 1.0 |
|  | Fragrance | 0.3 | 0.3 | 0.3 | 0.3 | 0.3 | 0.3 | 0.3 |
|  | Total (mass %) | 100.0 | 100.0 | 100.0 | 100.0 | 100.0 | 100.0 | 100.0 |
|  | A/C | 1.212 | 1.212 | 1.212 | 1.212 | 1.212 | 1.212 | 1.212 |
|  | B/C | 1.212 | 1.212 | 1.212 | 1.212 | 1.212 | 1.212 | 1.212 |
|  | (A + B)/C | 2.424 | 2.424 | 2.424 | 2.424 | 2.424 | 2.424 | 2.424 |
|  | Stability evaluation of sodium percarbonate | 5 | 4 | 4 | 4 | 4 | 4 | 4 |
|  | Solubility evaluation in water | 5 | 3 | 4 | 3 | 3 | 3 | 3 |
|  | Moldability evaluation of molded body | 5 | 4 | 4 | 4 | 4 | 4 | 4 |

Table 3 illustrates that in comparison among Examples 1 and 3 to 8, Examples 1 and 3 to 8, which contain as the component (B) a substance having a water absorbency of 106 or more in terms of a weight change rate, had a rating of 3 or more in all of the stability evaluation, solubility evaluation, and moldability evaluation.

Therefore, it was demonstrated that the stability of the percarbonate contained in the molded body, the solubility of the molded body, and the moldability of the molded body are all improved by blending, in the molded body, a substance having a water absorbency of less than 106 in terms of a weight change rate as the component (A) and a substance having a water absorbency of 106 or more in terms of a weight change rate as the component (B).

TABLE 4

|   | Component name | Example 9 | Example 10 | Example 11 | Example 12 |
|---|---|---|---|---|---|
| (A) | Crystalline cellulose | 1.00 | 10.00 | 35.00 | 40.00 |
| (B) | Acetic acid starch | 20.00 | 20.00 | 20.00 | 20.00 |
| (C) | Sodium percarbonate | 16.50 | 16.50 | 16.50 | 10.00 |
| (D) | p-Phenylenediamine sulfate | 13.00 | 13.00 | 13.00 | 13.00 |
|   | Toluene-2,5-diamine sulfate | 3.00 | 3.00 | 3.00 | 3.00 |
|   | m-Aminophenol sulfate | 1.00 | 1.00 | 1.00 | 1.00 |
| (E) | Magnesium stearate | 0.50 | 0.50 | 0.50 | 0.50 |
| (F) | Xanthan gum | 3.00 | 3.00 | 3.00 | 3.00 |
|   | Sodium carboxymethyl cellulose | 5.00 | 5.00 | 5.00 | 5.00 |
|   | Sodium sulfate | 34.75 | 25.75 | 0.75 | 2.25 |
|   | O-[2-Hydroxy-3-(trimethylammonio)propyl] guar gum chloride | 1.00 | 1.00 | 1.00 | 1.00 |
|   | Trisodium hydroxyethyl ethylenediamine triacetate dihydrate | 1.00 | 1.00 | 1.00 | 1.00 |
|   | Fragrance | 0.25 | 0.25 | 0.25 | 0.25 |
|   | Total (mass %) | 100.00 | 100.00 | 100.00 | 100.00 |
|   | A/C | 0.061 | 0.606 | 2.121 | 4.000 |
|   | B/C | 1.212 | 1.212 | 1.212 | 2.000 |
|   | (A + B)/C | 1.273 | 1.818 | 3.333 | 6.000 |
|   | Stability evaluation of sodium percarbonate | 3 | 3 | 5 | 5 |
|   | Solubility evaluation in water | 4 | 4 | 4 | 4 |
|   | Moldability evaluation of molded body | 3 | 4 | 5 | 5 |

Table 4 illustrates that in comparison among Examples 9 to 12, the rating was 3 or more in all of the stability evaluation, solubility evaluation, and moldability evaluation when the ratio (A)/(C) of the content of the component (A) to the content of the component (C) was 0.061 or more. When the ratio (A)/(C) was 0.061 or more, the ratings in the stability evaluation and moldability evaluation rose with an increase of the ratio (A)/(C).

Therefore, it was demonstrated that the stability of the percarbonate contained in the molded body and the moldability of the molded body are further improved when the ratio (A)/(C) in the molded body is in the range of 0.061 to 4.0.

TABLE 5

|   | Component name | Example 13 | Example 14 | Example 15 | Example 16 |
|---|---|---|---|---|---|
| (A) | Crystalline cellulose | 20.00 | 20.00 | 20.00 | 20.00 |
| (B) | Acetic acid starch | 1.00 | 10.00 | 35.00 | 40.00 |
| (C) | Sodium percarbonate | 16.50 | 16.50 | 16.50 | 10.00 |
| (D) | p-Phenylenediamine sulfate | 13.00 | 13.00 | 13.00 | 13.00 |
|   | Toluene-2,5-diamine sulfate | 3.00 | 3.00 | 3.00 | 3.00 |
|   | m-Aminophenol sulfate | 1.00 | 1.00 | 1.00 | 1.00 |
| (E) | Magnesium stearate | 0.50 | 0.50 | 0.50 | 0.50 |
| (F) | Xanthan gum | 3.00 | 3.00 | 3.00 | 3.00 |
|   | Sodium carboxymethyl cellulose | 5.00 | 5.00 | 5.00 | 5.00 |
|   | Sodium sulfate | 34.75 | 25.75 | 0.75 | 2.25 |
|   | O-[2-Hydroxy-3-(trimethylammonio)propyl] guar gum chloride | 1.00 | 1.00 | 1.00 | 1.00 |

TABLE 5-continued

| Component name | Example 13 | Example 14 | Example 15 | Example 16 |
|---|---|---|---|---|
| Trisodium hydroxyethyl ethylenediamine triacetate dihydrate | 1.00 | 1.00 | 1.00 | 1.00 |
| Fragrance | 0.25 | 0.25 | 0.25 | 0.25 |
| Total (mass %) | 100.00 | 100.00 | 100.00 | 100.00 |
| A/C | 1.212 | 1.212 | 1.212 | 2.000 |
| B/C | 0.061 | 0.606 | 2.121 | 4.000 |
| (A + B)/C | 1.273 | 1.818 | 3.333 | 6.000 |
| Stability evaluation of sodium percarbonate | 3 | 4 | 5 | 5 |
| Solubility evaluation in water | 3 | 3 | 5 | 5 |
| Moldability evaluation of molded body | 5 | 5 | 5 | 5 |

Table 5 illustrates that in comparison among Examples 13 to 16, the rating was 3 or more in all of the stability evaluation, solubility evaluation, and moldability evaluation when the ratio (B)/(C) of the content of the component (B) to the content of the component (C) was 0.061 or more. When the ratio (B)/(C) was 0.061 or more, the ratings in the stability evaluation and solubility evaluation rose with an increase of the ratio (B)/(C).

Therefore, it was demonstrated that the stability of the percarbonate contained in the molded body and the solubility of the molded body are further improved when the ratio (B)/(C) in the molded body is in the range of 0.061 to 4.0.

TABLE 6

| | Component name | Example 17 | Example 18 | Example 19 | Example 20 |
|---|---|---|---|---|---|
| (A) | Crystalline cellulose | 28.00 | 20.00 | 20.00 | 5.00 |
| (B) | Acetic acid starch | 28.00 | 20.00 | 20.00 | 5.00 |
| (C) | Sodium percarbonate | 7.00 | 10.00 | 30.00 | 35.00 |
| (D) | p-Phenylenediamine sulfate | 13.00 | 13.00 | 13.00 | 13.00 |
| | Toluene-2,5-diamine sulfate | 3.00 | 3.00 | 3.00 | 3.00 |
| | m-Aminophenol sulfate | 1.00 | 1.00 | 1.00 | 1.00 |
| (E) | Magnesium stearate | 0.50 | 0.50 | 0.50 | 0.50 |
| (F) | Xanthan gum | 3.00 | 3.00 | 3.00 | 3.00 |
| | Sodium carboxymethyl cellulose | 5.00 | 5.00 | 5.00 | 5.00 |
| | Sodium sulfate | 9.25 | 22.25 | 2.25 | 27.25 |
| | O-[2-Hydroxy-3-(trimethylammonio)propyl] guar gum chloride | 1.00 | 1.00 | 1.00 | 1.00 |
| | Trisodium hydroxyethyl ethylenediamine triacetate dihydrate | 1.00 | 1.00 | 1.00 | 1.00 |
| | Fragrance | 0.25 | 0.25 | 0.25 | 0.25 |
| | Total (mass %) | 100.00 | 100.00 | 100.00 | 100.00 |
| | A/C | 4.000 | 2.000 | 0.666 | 0.143 |
| | B/C | 4.000 | 2.000 | 0.666 | 0.143 |
| | (A + B)/C | 8.000 | 4.000 | 1.333 | 0.286 |
| | Stability evaluation of sodium percarbonate | 5 | 5 | 5 | 3 |
| | Solubility evaluation in water | 5 | 5 | 5 | 3 |
| | Moldability evaluation of molded body | 5 | 5 | 5 | 3 |

Table 6 illustrates that in comparison among Examples 17 to 20, the rating was 3 or more in all of the stability evaluation, solubility evaluation, and moldability evaluation when the ratio ((A)+(B))/(C) of the sum of the contents of the component (A) and the component (B) to the content of the component (C) was 0.286 or more. When ((A)+(B))/(C) was 0.286 or more, the ratings in the stability evaluation, solubility evaluation, and moldability evaluation rose with an increase of the ratio.

Therefore, it was demonstrated that the stability of the percarbonate contained in the molded body, the solubility of the molded body, and the moldability of the molded body are further improved when ((A)+(B))/(C) in the molded body is in the range of 0.286 to 8.0.

The above results demonstrated that the stability of the percarbonate, the solubility of the molded body, and the moldability of the molded body are all improved by blending, in the molded body that contains a percarbonate as the component (C), a substance having a water absorbency of less than 106 in terms of a weight change rate as the component (A) and a substance having a water absorbency of 106 or more in terms of a weight change rate as the component (B).

INDUSTRIAL APPLICABILITY

According to the present invention, it is possible to provide a molded body in which stability of a percarbonate, solubility of the molded body in water, and moldability of the molded body are improved.

The molded body of the present invention can be used for dyeing and bleaching/decoloring human body hair such as hair, beard, eyebrow hair, and leg hair. In addition, it may be used for dyeing and bleaching/decoloring body hair of animals such as pets.

In addition, the molded body of the present invention can be used for coloring in a beauty salon, a barber's shop, or the like or for self-coloring.

The invention claimed is:

1. A molded body comprising components (A) to (C) below:
   (A) a substance having a water absorbency of less than 106 in terms of a weight change rate;
   (B) a substance having a water absorbency of 106 or more in terms of a weight change rate;
   (C) a percarbonate;
   a lubricant; and
   a thickener,
   wherein a content of the thickener is 0.1 mass % or more and 20.0 mass % or less with respect to a mass of the molded body, and
   wherein the molded body is a tablet formed by tableting.

2. The molded body according to claim 1, wherein
   (A) is at least one selected from the group consisting of cellulose, a cellulose derivative, and sugar alcohol; and
   (B) is at least one selected from starches.

3. The molded body according to claim 1, wherein a ratio (A)/(C) of a content of the component (A) to a content of the component (C) is 0.1 to 4.00.

4. The molded body according to claim 1, wherein a ratio (B)/(C) of a content of the component (B) to a content of the component (C) is 0.1 to 4.00.

5. The molded body according to claim 1, wherein a ratio ((A)+ (B))/(C) of a sum of contents of the component (A) and the component (B) to a content of the component (C) is 0.3 to 8.0.

6. The molded body according to claim 1, wherein a content of the lubricant is 0.1 mass % or more and 5.0 mass % or less with respect to the mass of the molded body.

7. The molded body according to claim 1, wherein the lubricant is at least one selected from the group consisting of phyllosilicate mineral powder, silicon oxide, saturated fatty acid, esters, waxes, hardened vegetable oil, fat, and polyether.

8. The molded body according to claim 1, wherein the lubricant is at least one selected from the group consisting of talc, light anhydrous silicic acid, magnesium stearate, calcium stearate, sucrose fatty acid ester, magnesium carbonate, sodium benzoate, palmitic acid, sodium stearyl fumarate, beeswax, soybean hardened oil, cocoa butter, and polyethylene glycol.

9. The molded body according to claim 1, wherein the thickener is at least one selected from the group consisting of polysaccharides and water-soluble acrylic acid polymers.

10. The molded body according to claim 1, wherein the thickener is at least one selected from the group consisting of xanthan gum, sodium alginate, guar gum, cationized guar gum, a carboxyvinyl polymer, carrageenan, gellan gum, pectin, gum arabic, and locust bean gum.

* * * * *